United States Patent
Yamada et al.

(10) Patent No.: US 10,743,902 B2
(45) Date of Patent: Aug. 18, 2020

(54) VIBRATING BODY UNIT AND ULTRASONIC PROBE

(71) Applicant: OLYMPUS CORPORATION, Hachioji-shi, Tokyo (JP)

(72) Inventors: Masashi Yamada, Sagamihara (JP); Hideto Yoshimine, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 324 days.

(21) Appl. No.: 15/650,475

(22) Filed: Jul. 14, 2017

(65) Prior Publication Data

US 2017/0311976 A1 Nov. 2, 2017

Related U.S. Application Data

(63) Continuation of application No. PCT/JP2016/050798, filed on Jan. 13, 2016.

(30) Foreign Application Priority Data

Jan. 15, 2015 (JP) ................... 2015-006033

(51) Int. Cl.
*A61B 17/32* (2006.01)
*A61B 18/00* (2006.01)
(Continued)

(52) U.S. Cl.
CPC ...... *A61B 17/320092* (2013.01); *A61B 18/00* (2013.01); *B06B 1/00* (2013.01);
(Continued)

(58) Field of Classification Search
CPC ........ A61B 17/320068; A61B 17/2204; A61B 2017/320069; A61B 2017/32007;
(Continued)

(56) References Cited

U.S. PATENT DOCUMENTS

2006/0235306 A1 10/2006 Cotter et al.
2007/0257083 A1* 11/2007 Narasimalu ............... B06B 3/00
228/1.1
(Continued)

FOREIGN PATENT DOCUMENTS

CN 102573983 B 5/2015
CN 105722470 A 6/2016
(Continued)

OTHER PUBLICATIONS

Jan. 28, 2019 Office Action issued in Chinese Patent Application No. 201680005970.8.
(Continued)

*Primary Examiner* — Linda C Dvorak
*Assistant Examiner* — Annabeth E Rodriguez
(74) *Attorney, Agent, or Firm* — Oliff PLC

(57) ABSTRACT

A vibrating body unit includes a vibration generator, a vibration transmitter and first amplitude enlarger. The vibration generator generates ultrasonic vibration whose amplitude has a predetermined correlation with a frequency. The vibration transmitter has a proximal end and a distal end while the vibration generator is attached from a proximal side, and transmits the ultrasonic vibration to a distal side in a longitudinal axis direction. At least one first amplitude enlarger is provided in the vibration transmitter, and enlarges the amplitude of the ultrasonic vibration at a first amplitude enlargement rate in a direction of transmission of the ultrasonic vibration, the first amplitude enlargement rate having a correlation with the frequency opposite to the predetermined correlation.

13 Claims, 9 Drawing Sheets

(51) Int. Cl.
B06B 1/00 (2006.01)
B06B 3/02 (2006.01)
*A61B 17/22* (2006.01)

(52) U.S. Cl.
CPC ...... B06B 3/02 (2013.01); *A61B 2017/22018* (2013.01); *A61B 2017/320088* (2013.01); *A61B 2017/320089* (2017.08); *A61B 2017/320095* (2017.08)

(58) Field of Classification Search
CPC ....... A61B 2017/320072; A61B 2017/320084; A61B 2017/320089; A61B 2018/0019; A61B 2018/00845; A61B 2018/0088; A61N 7/00
USPC .................................................. 606/27, 169
See application file for complete search history.

(56) References Cited

U.S. PATENT DOCUMENTS

| | | |
|---|---|---|
| 2008/0194999 A1 | 8/2008 | Yamaha et al. |
| 2008/0294051 A1 | 11/2008 | Koshigoe et al. |
| 2011/0040212 A1 | 2/2011 | Dietz et al. |
| 2011/0040213 A1* | 2/2011 | Dietz ...................... A61N 7/00 601/2 |
| 2013/0253557 A1 | 9/2013 | Urich et al. |
| 2016/0199881 A1 | 7/2016 | Akagane |

FOREIGN PATENT DOCUMENTS

| | | |
|---|---|---|
| JP | 2001-161706 A | 6/2001 |
| JP | 2008-289876 A | 12/2008 |

OTHER PUBLICATIONS

Mar. 22, 2016 International Search Report issued in International Patent Application No. PCT/JP2016/050798.

Jul. 3, 2018 Extended European Search Report issued in Patent Application No. 16737361.2.

Jul. 30, 2019 Office Action issued in Chinese Patent Application No. 201680005970.8.

\* cited by examiner

VIBRATING BODY UNIT AND ULTRASONIC PROBE

CROSS-REFERENCE TO RELATED APPLICATIONS

This is a Continuation Application of PCT Application No. PCT/JP2016/050798, filed Jan. 13, 2016 and based upon and claiming the benefit of priority from prior Japanese Patent Application No. 2015-006033, filed Jan. 15, 2015, the entire contents of which are incorporated herein by reference.

BACKGROUND OF THE INVENTION

1. Field of the Invention

The present invention relates to a vibrating body unit and an ultrasonic probe applicable to an ultrasonic treatment instrument used in, for example, a surgical operation.

2. Description of the Related Art

An ultrasonic treatment instrument for treating a subject using ultrasonic vibration is known (see, for example, Jpn. Pat. Appln. KOKAI Publication No. 2008-289876). This type of treatment instrument includes a vibration generating unit (transducer) that generates ultrasonic vibration, and an ultrasonic probe replaceably attached to the vibration generating unit. The energy of the ultrasonic vibration is transmitted through the ultrasonic probe, and is converted into heat energy at a portion (distal portion) at which the ultrasonic probe contacts the subject.

Since the ultrasonic probe directly contacts the subject, the ultrasonic probe is frequently replaced. That is, the vibration generating unit is reusable, whereas the ultrasonic probe is disposable.

BRIEF SUMMARY OF THE INVENTION

According to one aspect of the invention, a vibrating body unit including: a vibration generator which is configured to generate ultrasonic vibration, amplitude of the generated ultrasonic vibration being changed in such a manner that the amplitude has a predetermined correlation with a frequency; a vibration transmitting portion which has a proximal end and a distal end, and to which the vibration generator is attached on a proximal side, the vibration transmitting portion being configured to transmit the ultrasonic vibration to a distal side in a longitudinal axis direction; and at least one first amplitude enlarger which is provided in the vibration transmitting portion, and which is configured to enlarge the amplitude of the ultrasonic vibration at a first amplitude enlargement rate in a direction of transmission of the ultrasonic vibration, the first amplitude enlargement rate having a correlation with the frequency opposite to the predetermined correlation.

According to one another aspect of the invention, an ultrasonic probe which is separably connected to a vibration generating unit including a vibration generator, the vibration generator being configured to ultrasonic vibration, amplitude of the generated ultrasonic vibration being changed in such a manner that the amplitude has a predetermined correlation with a frequency, the ultrasonic probe including: a vibration transmitting member which has a proximal end and a distal end, and which is configured to transmit, to a distal side, the ultrasonic vibration transmitted from the vibration generating unit to the proximal end in a longitudinal axis direction; and an amplitude enlarger which is provided in the vibration transmitting member, and which is configured to enlarge the amplitude of the ultrasonic vibration at an amplitude enlargement rate in a direction of transmission of the ultrasonic vibration, the amplitude enlargement rate having a correlation with the frequency opposite to the predetermined correlation.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
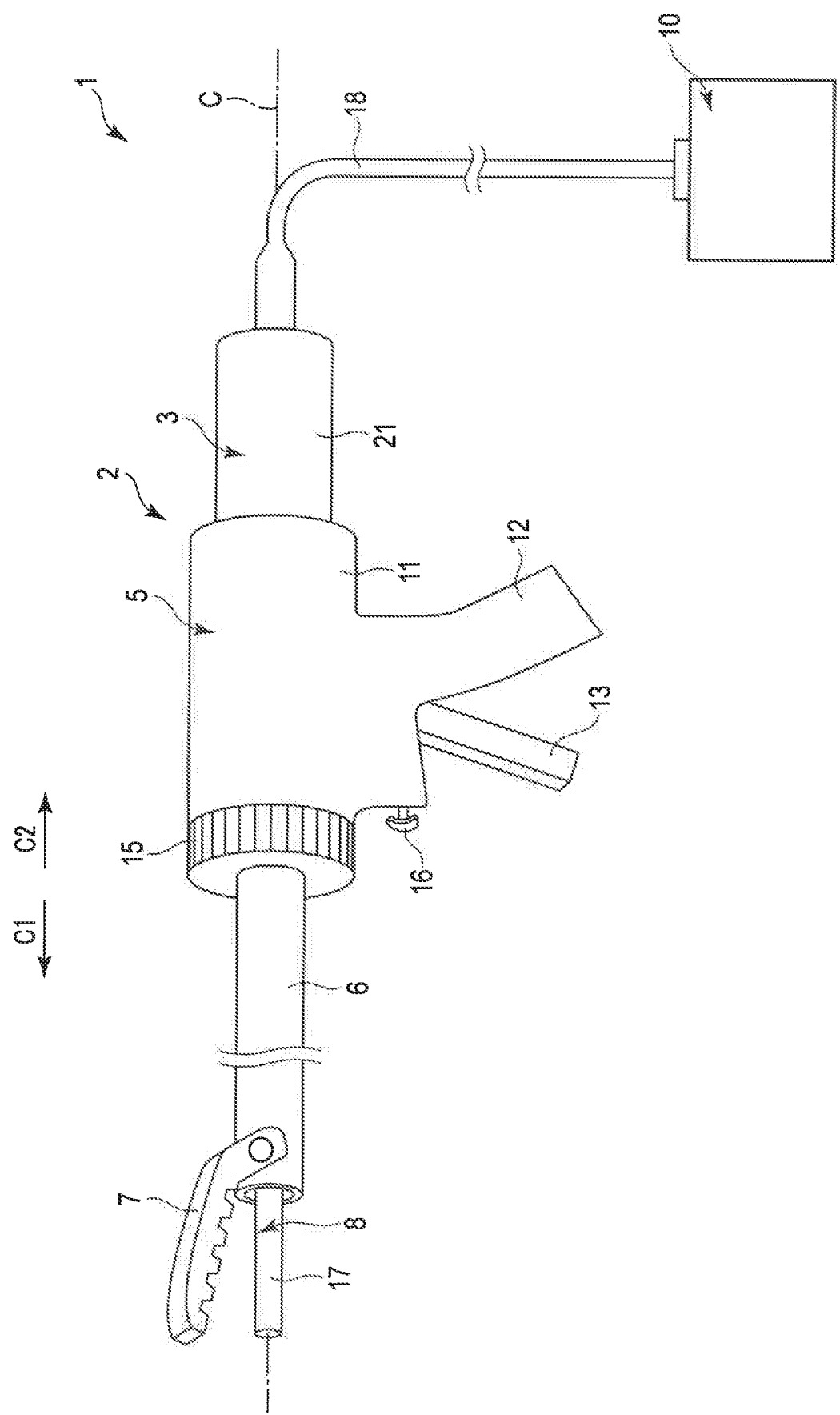
FIG. 1 is a schematic view showing an exemplary ultrasonic treatment system according to an embodiment.

FIG. 1 is a schematic view showing an exemplary ultrasonic system according to an embodiment. As shown in FIG. 1, an ultrasonic treatment system 1 includes an ultrasonic treatment instrument 2. The ultrasonic treatment instrument 2 has a longitudinal axis C. In the description below, a direction parallel to the longitudinal axis C is defined as a longitudinal axis direction. One side of the longitudinal axis direction is a distal side (side of the arrow C1 in FIG. 1), and a side opposite to the distal side is a proximal side (side of the arrow C2 in FIG. 1).

The ultrasonic treatment instrument 2 includes a transducer unit 3, a hold unit 5 which can be held by an operator, etc., a sheath 6, a jaw (gripping member) 7, and an ultrasonic probe (distal-side vibration transmitting member) 8. The hold unit 5 includes a case body portion 11, a stationary handle 12, and a movable handle 13. The case body portion 11 extends along the longitudinal axis C. The stationary handle 12 extends from the case body portion 11 toward a certain direction intersecting the longitudinal axis C.

The movable handle 13, which is an opening/closing operation input portion, is rotatably attached to the case body portion 11. When the movable handle 13 is rotated with respect to the case body portion 11, the movable handle 13 is closed or open relative to the stationary handle 12.

A rotating operation knob 15, which is a rotating operation input portion, is coupled to the distal side of the case body portion 11. The rotating operation knob 15 is rotatable around the longitudinal axis C with respect to the case body portion 11. An energy operation button 16, which is an energy operation input portion, is attached to the case body portion 11, preferably near the movable handle 13.

The sheath 6 is coupled to the hold unit 5 in a state of being inserted from the distal side into the rotating operation knob 15 and the case body portion 11. The jaw 7 is rotatably attached to the distal portion of the sheath 6. The ultrasonic probe 8 extends toward the distal side from the inside of the case body portion 11 through the inside of the sheath 6.

In the embodiment, the ultrasonic probe (vibration transmitting member body) 8 extends from a proximal end to a distal end along the longitudinal axis C. The central axis of the ultrasonic probe 8 coincides with the longitudinal axis C. A treatment portion 17 is provided in a distal portion of the ultrasonic probe 8. The ultrasonic probe 8 is inserted through the sheath 6, with the treatment portion 17 protruding from a distal end of the sheath 6 toward the distal side.

By an opening or closing motion of the movable handle 13 with respect to the stationary handle 12, the movable portion (not shown) provided inside the sheath 6 moves along the longitudinal axis C, and the jaw 7 is rotated. By being rotated, the jaw 7 performs an opening or a closing motion with respect to the treatment portion 17 of the ultrasonic probe 8. The sheath 6, the jaw 7, and the ultrasonic probe 8 are rotatable about the longitudinal axis C with respect to the case body portion 11, integrally with the rotating operation knob 15.

The transducer unit 3 includes a transducer case 21, which forms the exterior of the transducer unit 3. The transducer case 21 is coupled to the hold unit 5 in a state of being inserted from the proximal side into the case body portion 11. The transducer case 21 is separably coupled to the sheath 6 inside the case body portion 11. One end of a cable 18 is connected to the transducer case 21. In the ultrasonic treatment system 1, the other end of the cable 18 is detachably connected to an energy source unit 10.

The energy source unit 10 is, for example, an energy control device (electric power source device) for medical use, and includes, for example, an electric power source and an alternating-current conversion circuit (neither is shown). The energy source unit 10 includes a controller (not shown) that controls an output of the electric power (electric energy). The controller includes a storage (not shown), such as a memory, and a processor including a central processing unit (CPU), an application-specific integrated circuit (ASIC), or the like.

Figure 2:
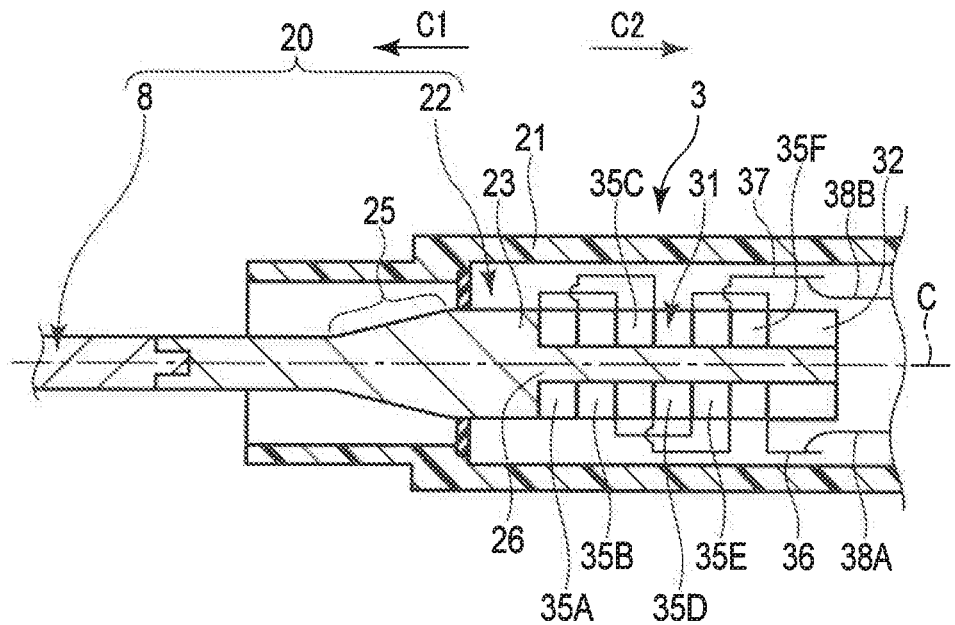
FIG. 2 is a cross-sectional view schematically showing an exemplary transducer unit according to the embodiment.

FIG. 2 shows a configuration of the transducer unit 3. A further detailed explanation will be given below, with reference to FIGS. 1 and 2. A vibration generating unit (ultrasonic transducer) 22 is provided inside the transducer case 21 of the transducer unit 3. The vibration generating unit 22 is supported by the transducer case 21. The vibration generating unit 22 includes a front mass (proximal-side vibration transmitting member) 23. In the embodiment, the central axis of the front mass (transmitting member) 23 coincides with the longitudinal axis C, and the front mass 23 extends from the proximal end to the distal end along the longitudinal axis C.

The distal end of the front mass 23 is separably connected to the proximal end of the ultrasonic probe 8 inside the case body portion 11. Since the front mass 23 is connected to the ultrasonic probe 8, the ultrasonic probe 8 is coupled to the distal side of the vibration generating unit 22. The vibration generating unit 22 coupled to the ultrasonic probe 8 is rotatable around the longitudinal axis C with respect to the case body portion 11, integrally with the ultrasonic probe 8.

The front mass 23 includes a horn (cross-sectional reduction portion) 25. In the horn 25, a cross-sectional area perpendicular to the longitudinal axis C of the front mass 23 is reduced toward the distal side. Moreover, an element attachment portion 26 is provided on the proximal side with respect to the horn 25 of the front mass 23.

In the vibration generating unit 22, an element unit 31 (vibration generator) and a back mass 32 are attached to the element attachment portion 26. The back mass 32 is a proximal-side fixing member. The front mass 23 is a distal-side fixing member. The element unit 31 and the back mass 32 are formed in the shape of a ring having the longitudinal axis C as the central axis. The element attachment portion 26 of the front mass 23 is inserted through the element unit 31 and the back mass 32 in this order, allowing the element unit 31 and the back mass 32 to be attached to the element attachment portion 26.

The element unit 31 includes a proximal end and a distal end, and extends from the proximal end to the distal end along the longitudinal axis C. In the present embodiment, the axis of the element unit 31 coincides with the longitudinal axis C. The back mass 32 abuts on the proximal end of the element unit 31, and the front mass 23 abuts on the distal end of the element unit 31. That is, the back mass 32 abuts on the element unit 31 from the proximal side, and the front mass 23 abuts on the element unit 31 from the distal side. Thus, the element unit 31 is sandwiched between the back mass (proximal-side fixing member) 32 and the front mass (distal-side fixing member) 23, in the longitudinal direction parallel to the longitudinal axis C.

Figure 3:
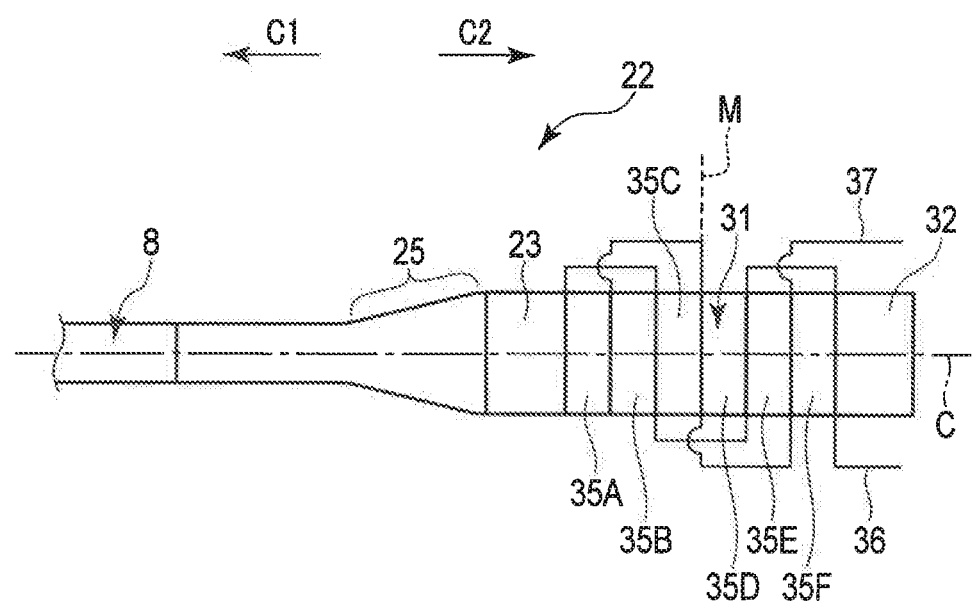
FIG. 3 is a schematic view showing an exemplary vibration generating unit according to the embodiment.

FIG. 3 shows a configuration of the vibration generating unit 22. As shown in FIGS. 2 and 3, the element unit 31 includes a plurality of (six in the present embodiment) piezoelectric elements 35A-35F, a first electrode member 36, and a second electrode member 37. The piezoelectric elements 35A, 35B, 35C, 35D, 35E, and 35F are arranged in this order from the distal side toward the proximal side of the element unit 31, along the longitudinal axis direction of the vibration generating unit 22.

Each of the piezoelectric elements 35A-35F is sandwiched between the first electrode member 36 and the second electrode member 37. The first electrode member 36 is connected to one end of an electrical wiring portion 38A. The second electrode member 37 is connected to one end of an electrical wiring portion 38B. The electrical wiring portions 38A and 38B extend through the inside of the cable 18. The other end of the electrical wiring portion 38A and the other end of the electrical wiring portion 38B are electrically connected to the electric power source of the energy source unit 10 and the alternating-current conversion circuit (neither is shown).

The hold unit 5 includes therein a switch portion (not shown). The switch portion is electrically connected to a controller (not shown) of the energy source unit 10 via a signal path portion (not shown) extending through the transducer unit 3 and the inside of the cable 18. The open/close state of the switch portion is switched in response to an input of an energy operation made via the energy operation button 16. By detecting the open/close state of the switch portion, the controller detects the input of the energy operation made via the energy operation button 16.

When an input of an energy operation is detected, the energy source unit 10 outputs electric power (alternating-current power). Thereby, a voltage is applied between the first electrode member 36 and the second electrode member 37, and driving electric power (vibration generating electrical energy) is supplied to each of the piezoelectric elements 35A-35F. This causes the piezoelectric elements 35A-35F to generate ultrasonic vibration.

The ultrasonic vibration is transmitted from the element unit 31 through the front mass 23 toward the distal side, and transmitted to the ultrasonic probe 8. In that case, the horn 25 enlarges the amplitude of the vibration.

The ratio of the output amplitude to the input amplitude is defined as an amplitude enlargement rate. The input amplitude to the horn 25 is an amplitude at a position on the proximal side of the horn 25, and the output amplitude is an amplitude at a position on the distal side of the horn 25. The amplitude enlargement rate is closely correlated with the vibration frequency (resonance frequency Fr). In the embodiment, the characteristic of the amplitude enlargement rate to increase as the vibration frequency increases will be referred to as a positive correlation. Conversely, the characteristic of the amplitude enlargement rate to decrease as the vibration frequency increases will be referred to as a negative correlation.

An ultrasonic vibration that has reached the ultrasonic probe 8 is transmitted through the ultrasonic probe 8 toward the treatment portion 17. When the treatment portion 17 contacts a subject while ultrasonically vibrating, the vibration energy is converted into heat energy, allowing a surgical treatment such as a simultaneous treatment of incision and coagulation to be performed.

By connecting the ultrasonic probe 8 to the vibration generating unit 22, an ultrasonic probe unit (vibrating body unit) 20 is formed. The ultrasonic probe unit 20 vibrates in parallel to the longitudinal axis C (longitudinal axis direction) as the ultrasonic vibration is transmitted toward the treatment portion 17. In the embodiment, a proximal end of the back mass 32 (proximal end of the front mass 23) is a proximal end of the ultrasonic probe unit 20, and a distal end of the ultrasonic probe 8 is a distal end of the ultrasonic probe unit 20. The ultrasonic probe 8 and a part of the front mass 23 form a vibration transmitting portion. The vibration transmitting portion transmits the ultrasonic vibration generated by the piezoelectric elements 35A-35F from the proximal side to the distal side in the longitudinal axis direction.

In the above-described configuration of the ultrasonic probe unit (vibrating body unit) 20, the ultrasonic probe 8 is separable from the vibration generating unit 22; however, the configuration is not limited thereto. For example, the ultrasonic probe unit (vibrating body unit) 20 may be configured in such a manner that the vibration transmitting portion (the ultrasonic probe 8 and the front mass 23) is integrally formed, without the ultrasonic probe 8 and the vibration generating unit 22 being separated from each other. Next, a plurality of examples of the present invention will be described based on the above configuration.

First Example

Figure 4:
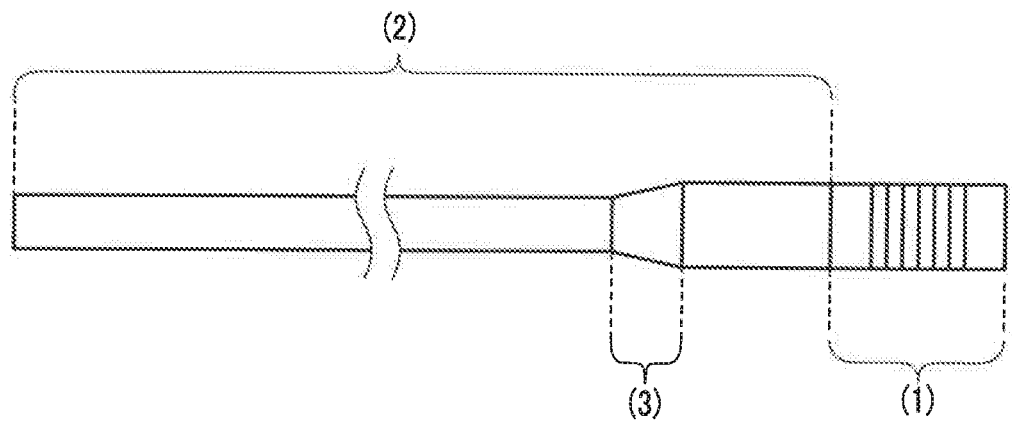
FIG. 4 is a schematic view showing an exemplary ultrasonic probe unit according to a first example.

FIG. 4 is a schematic view showing an exemplary ultrasonic probe unit according to a first example. The reference numeral (1) in FIG. 4 denotes a vibration generator including a part of a front mass 23, an element unit 31, and a back mass 32. A vibration transmitting portion (2) is provided on the distal side with respect to the vibration generator, and the vibration transmitting portion (2) includes a horn (3). The vibration transmitting portion (2) includes a part of the front mass 23 other than the part forming the vibration generator (1), and an ultrasonic probe 8. In the present example, the position where a vibration generating unit 22 (front mass 23) is supported by a transducer case 21 is a boundary between the vibration generator (1) and the vibration transmitting portion (2) in the longitudinal axis direction, and is a distal end of the vibration generator (1) (proximal end of the vibration transmitting portion (2)).

The horn (3), which has an amplitude enlargement rate, enlarges the amplitude of ultrasonic vibration transmitted from a vibration input end and outputs it from a vibration output end. It is known that the correlation between the amplitude enlargement rate and the vibration frequency changes according to the positional relationship between a node (vibration nodes) of ultrasonic vibration and a horn. A detailed explanation will be given below.

Figure 5:
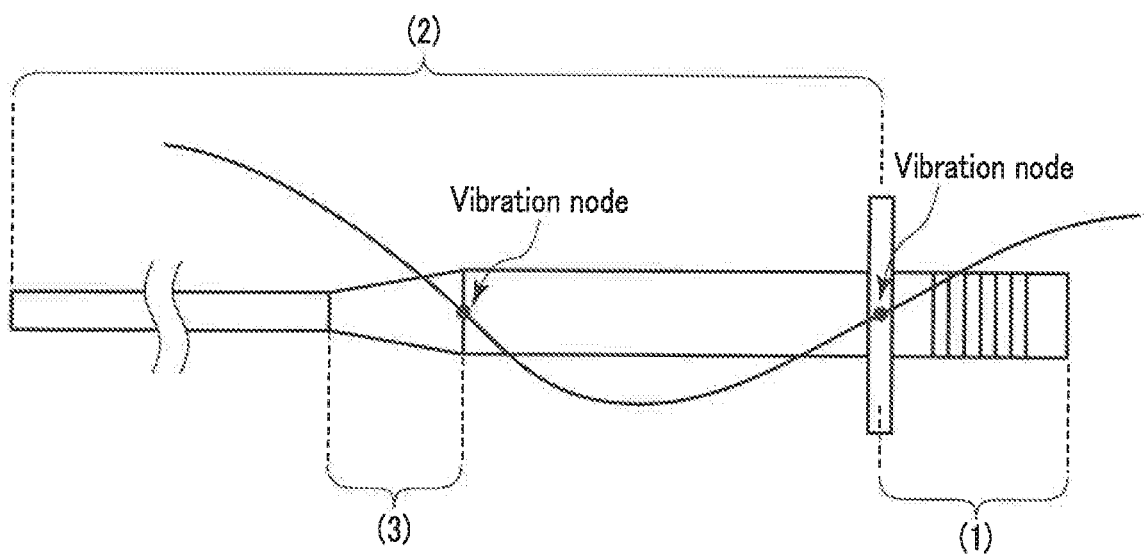
FIG. 5 is a schematic view showing an exemplary positional relationship between vibration nodes and a horn according to a comparative example.

FIG. 5 is a schematic view illustrating an exemplary positional relationship between vibration nodes and a horn according to a comparative example. In the comparative example, a vibration generator (1), a vibration transmitting portion (2), and a horn (3) are provided, as in the present example. In the comparative example shown in FIG. 5, one of vibration nodes of ultrasonic vibration occurs at the distal end of the vibration generator (1), and a vibration node adjacent to this vibration node occurs at the vibration input end of the horn (3). In this state, the trend of changes in amplitude at the vibration generator (1) of a Bolt-clamped Langevin type Transducer (BLT) relative to the frequency is the same as the trend of changes in amplitude enlargement rate at the horn (3) relative to the frequency. That is, the correlation between the frequency (resonance frequency Fr) and changes in amplitude (vibration speed) at the vibration generator (1) has a trend similar to that of the correlation between the frequency and changes in the amplitude enlargement rate at the horn (3). A vibration node that occurs at the vibration input end of the horn (3) is located on the distal side by approximately a half-wavelength of ultrasonic vibration from a vibration node that occurs at the distal end of the vibration generator (1).

Figure 6:
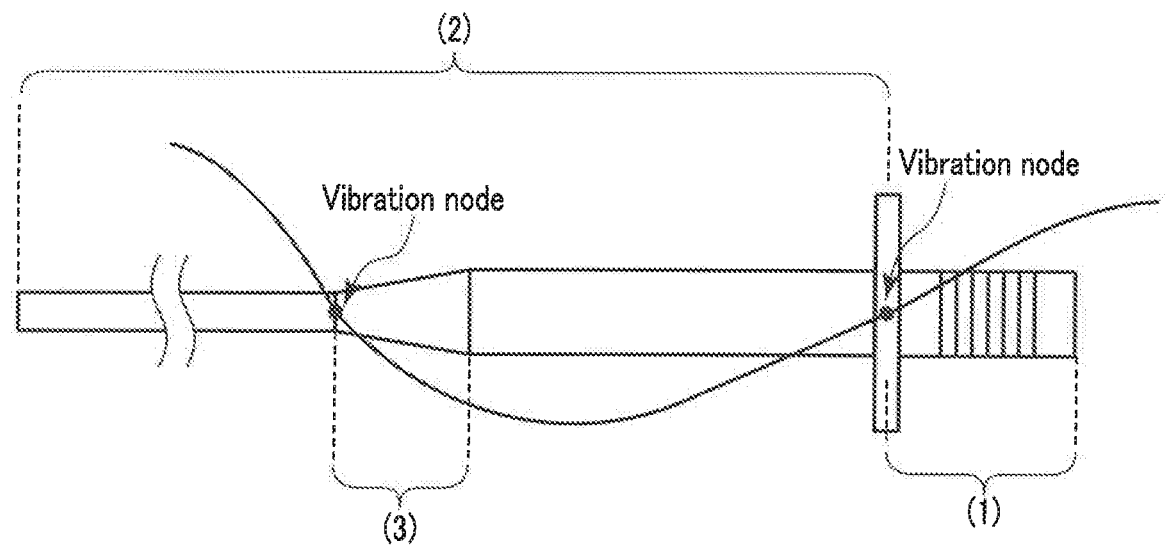
FIG. 6 is a schematic view showing an exemplary positional relationship between vibration nodes and a horn according to the first example.

FIG. 6 is a schematic view showing an exemplary positional relationship between vibration nodes and a horn according to the first example. In the present example shown in FIG. 6, one of vibration nodes of ultrasonic vibration occurs at the distal end of the vibration generator (1), but a vibration node adjacent to this vibration node occurs at the vibration output end of the horn (3), unlike FIG. 5 (comparative example). In this state, the trend of changes in amplitude at the vibration generator (1) relative to the frequency is opposite to the trend of changes in amplitude enlargement rate at the horn (3) relative to the frequency. That is, the correlation between the frequency (resonance frequency Fr) and changes in amplitude (vibration speed) at the vibration generator (1) is opposite to the correlation between the frequency and the amplitude enlargement rate at the horn (3). Thus, when viewed as a whole vibration system, the correlations act to cancel each other out. A vibration node that occurs at the vibration output end of the horn (3) is located on the distal side by approximately a half-wavelength of ultrasonic vibration from a vibration node that occurs at the distal end (the position where the front mass 23 is supported by the transducer case 21 in the present example) of the vibration generator (1).

Figure 7:
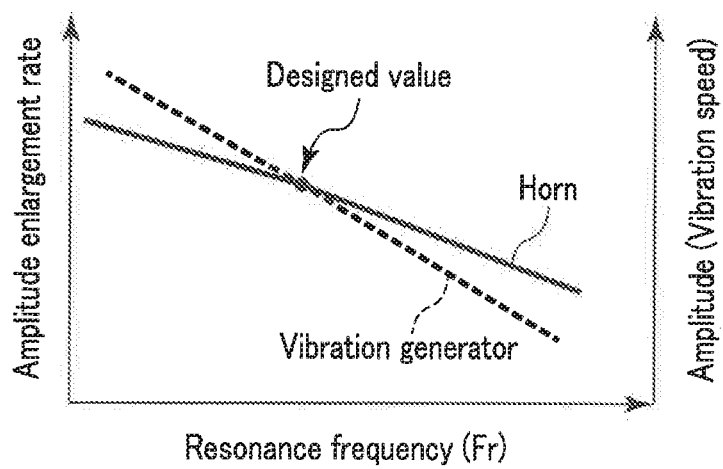
FIG. 7 shows a trend of changes in amplitude enlargement rate at the horn and a trend of changes in amplitude (vibration speed) at a vibration generator relative to a resonance frequency (Fr), under the conditions shown in FIG. 5.

FIG. 7 shows a trend of changes in amplitude enlargement rate at the horn (3) and a trend of changes in amplitude (vibration speed) at the vibration generator (1) relative to the resonance frequency (Fr), under the conditions shown in FIG. 5 (comparative example). The amplitude enlargement rate (solid line) of the horn (3) shows a trend similar to that of the amplitude (dotted line) of the vibration generator (1). That is, both have a negative correlation with the frequency, and increase, in combination, the slope of correlation with the frequency. Thus, in the comparative example, the vibration speed at the distal end of the ultrasonic probe 8 sensitively changes as the vibration frequency (resonance frequency Fr) changes, which is not preferable.

Figure 8:
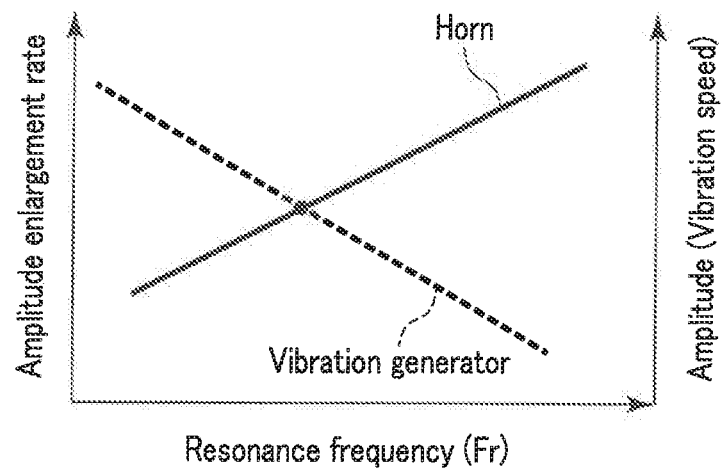
FIG. 8 shows a trend of changes in amplitude enlargement rate at the horn and a trend of changes in amplitude (vibration speed) at a vibration generator relative to a resonance frequency (Fr), under the conditions shown in FIG. 6.

FIG. 8 shows a trend of changes in amplitude enlargement rate (transformation ratio) at the horn (3) and a trend of changes in amplitude (vibration speed) at the vibration generator (1) relative to the resonance frequency (Fr), under the conditions shown in FIG. 6 (present example). Unlike FIG. 7, the amplitude enlargement rate (solid line) of the horn (3) shows a trend opposite to that of the amplitude (dotted line) of the vibration generator (1). That is, the changes in amplitude of the vibration generator (1) have a negative correlation with the frequency, whereas the amplitude enlargement rate of the horn (3) has a positive correlation with the frequency.

When such characteristics are combined, the slope of correlation with the frequency (resonance frequency Fr) comes close to flat (zero) as a whole. Thus, the vibration speed at the distal end of the ultrasonic probe 8 falls within a stable range, even when the vibration frequency changes.

Figure 9:
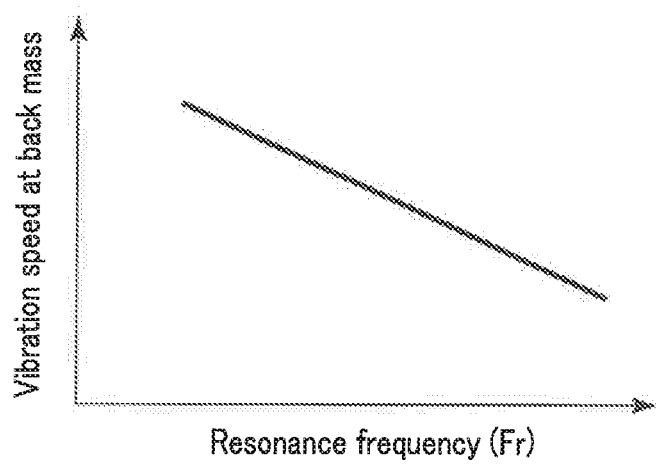
FIG. 9 shows an exemplary relationship of the vibration speed at a back mass with the resonance frequency, according to the first example.

A further detailed explanation will be given below, with reference to FIGS. 9-11. As shown in FIG. 9, the vibration speed at the vibration origin point (back mass) decreases as the frequency (resonance frequency Fr) increases. In an existing ultrasonic probe unit (as in the comparative example shown in FIG. 5), vibration is transmitted via a horn at which the amplitude enlargement rate (transformation ratio) has a negative correlation with the frequency, as shown by the dotted line in FIG. 10. This causes the vibration speed at a distal end of the vibration transmitting member to abruptly change as the frequency (resonance frequency Fr) changes, as shown by the dotted line in FIG. 11.

Figure 10:
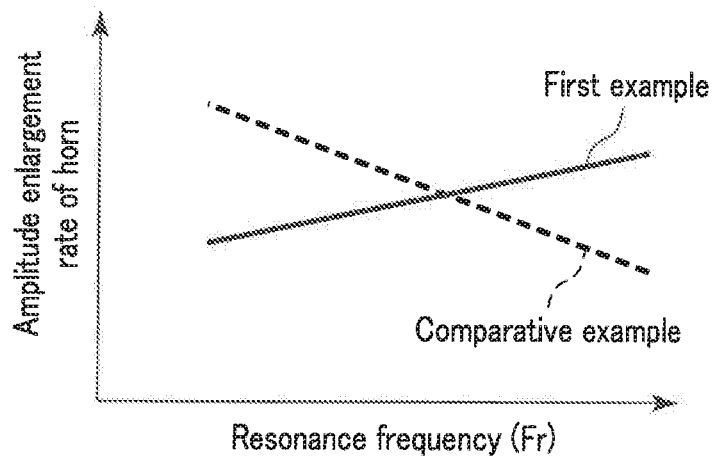
FIG. 10 shows a relationship of the amplitude enlargement rate (transformation ratio) of the horn with the resonance frequency, based on comparison between the comparative example and the first example.
Figure 11:
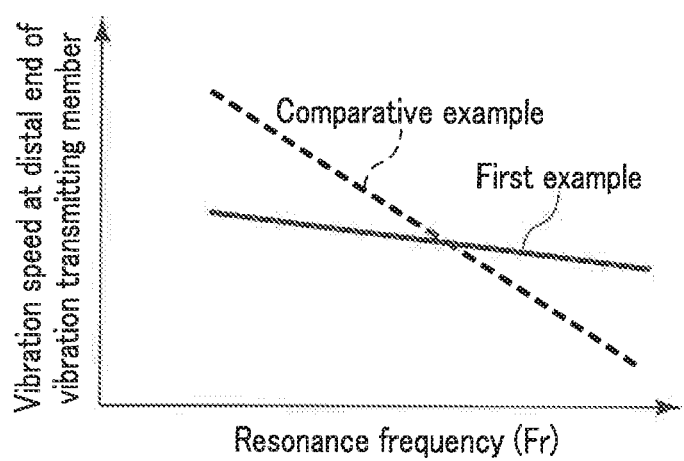
FIG. 11 shows a relationship of the vibration speed at a distal end of a vibration transmitting member with the resonance frequency, based on comparison between the comparative example and the first example.

In the present embodiment, on the other hand, the horn of the vibration transmitting member has a correlation opposite to that of the existing horn, as shown by the solid line in FIG. 10. It is thus possible to keep the changes in vibration speed at the distal end of the vibration transmitting member relative to the changes in frequency (resonance frequency Fr) within a narrower range, as shown by the solid line in FIG. 11.

As described above, according to the present example, the correlation of the amplitude at the vibration generator (1) with the vibration frequency and the correlation of the amplitude enlargement rate at the horn (3) of the vibration transmitting portion (2) with the vibration frequency are mutually opposite to each other. This is achieved by appropriately controlling the positions where vibration nodes occur. That is, in the present example, the position where each horn (3) is formed is set in such a manner that, when one of vibration nodes of ultrasonic vibration occurs at the distal end of the vibration generator (1) (the position where the front mass is supported), a vibration node adjacent to this vibration node occurs at the vibration output end of the horn (3) provided in the vibration transmitting portion (2). This allows the changing trend of the vibration speed at the vibration generator (1) relative to the frequency and the changing trend of the amplitude enlargement rate at each horn (3) relative to the frequency to be canceled each other out, thus suppressing changes in vibration speed in the distal portion of the vibration transmitting portion (2), even when the vibration frequency changes according to difference in individual ultrasonic probes. It is thus possible to reduce variability in vibration speed in the distal portion of the vibration transmitting portion (2) caused by fluctuations in vibration frequency (resonance frequency Fr) to a permissible range.

Modification of First Example

This example can be modified as will be described below. For example, one or more horns that have a correlation of changes in amplitude enlargement rate with the frequency opposite to a correlation of changes in amplitude (vibration speed) at the vibration generator with the frequency may be provided, in such a manner that the slope of correlation of the vibration speed at the distal end of the vibration transmitting portion with the frequency comes close to flat (zero) as a whole.

Figure 12:
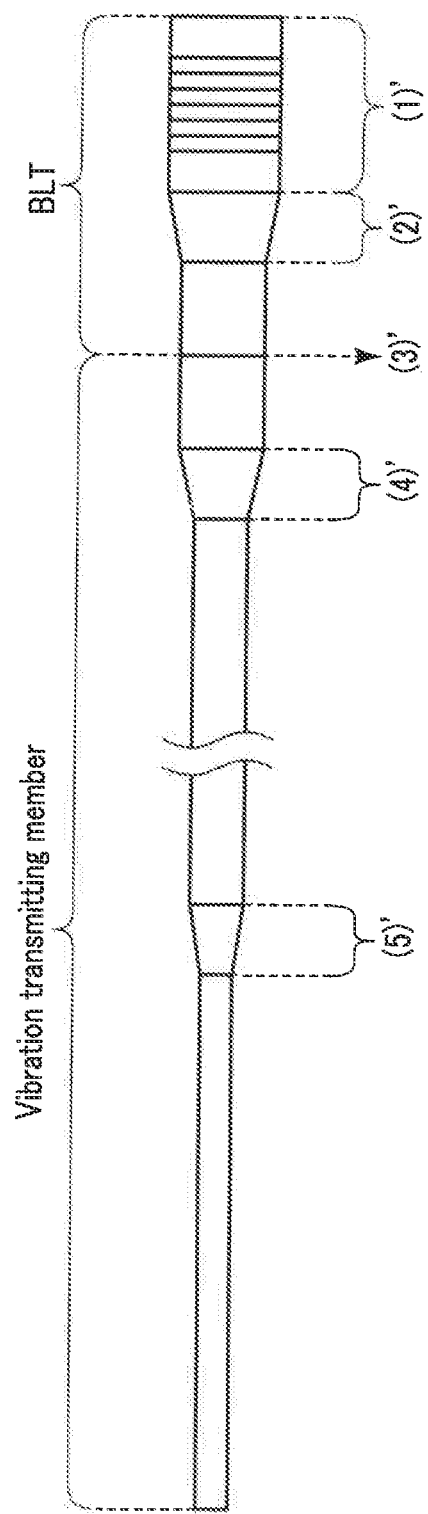
FIG. 12 is a schematic view showing an exemplary ultrasonic probe unit according to a modification of the first example.

FIG. 12 is a schematic view showing an exemplary ultrasonic probe unit according to a modification in which a plurality of horns are provided. The ultrasonic probe unit is configured by attaching a vibration transmitting member to a Bolt-clamped Langevin type transducer (BLT) as a vibration generating unit 22. A probe is connected to a distal end of the BLT at an attachment portion (3)', and the frequency characteristic of the vibration system is changed according to the connected probe.

The reference numeral (1)' of FIG. 12 denotes a vibration generator including a part of a front mass 23, an element unit 31, and a back mass 32. A plurality of horns (2)', (4)', and (5)', for example, may be formed in this order on the distal side, with respect to the vibration generator (1)'. In the present modification, a distal end of the vibration generator (1)' is continuous with a proximal end (vibration input end) of the horn (2)', and the position where a vibration generating unit 22 (front mass 23) is supported by a transducer case 21 is a boundary between the vibration generator (1)' and the horn (2)' in the longitudinal axis direction. In the present modification, the BLT includes one horn (2)'. The horn (2)' corresponds to, for example, the horn 25 (see FIGS. 2 and 3). The vibration transmitting member includes a body shaped into a rod, and a plurality of horns (4)' and (5)' as an amplitude enlarger formed in the body. The horns (2)', (4)', and (5) have respective amplitude enlargement rates, enlarges the amplitude of ultrasonic vibration transmitted from a vibration input end, and outputs it from a vibration output end. It is known that the correlation between the amplitude enlargement rate and the vibration frequency changes according to the positional relationship between a node (vibration node) of ultrasonic vibration and a horn. A detailed explanation will be given below.

Figure 13:
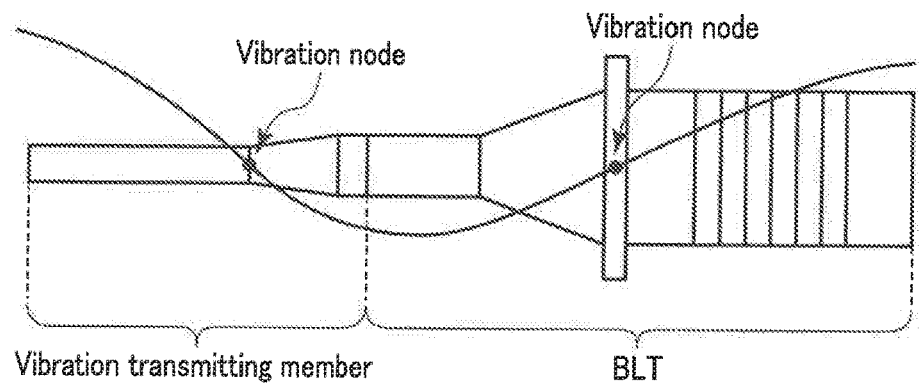
FIG. 13 is a schematic view showing an exemplary positional relationship between vibration nodes and horns according to the modification of the first example.

FIG. 13 is a schematic view showing an exemplary positional relationship between vibration nodes and horns according to the present modification. In FIG. 13, one of vibration nodes of ultrasonic vibration occurs at a vibration input end of a horn (e.g., (2)' of FIG. 12) of the BLT, but a vibration node adjacent to this vibration node occurs at a vibration output end of a horn (e.g., (4)' of FIG. 12) of the vibration transmitting member. In this state, the trend of changes in amplitude at the vibration generator (1)' of the BLT relative to the frequency is opposite to the trend of changes in amplitude enlargement rate at at least one of the horns (2)', (4)', and (5)' relative to the frequency. That is, the correlation between the frequency and the change in amplitude is opposite to the correlation between the frequency and the amplitude enlargement rate. Thus, when viewed as a whole vibration system, the correlations act to cancel each other out. In FIG. 12, for example, the amplitude enlargement rate of the horn (2)' may have a negative correlation with the frequency, the amplitude enlargement rate of the horn (4)' may have a negative correlation with the frequency, and the amplitude enlargement rate of the horn (5)' may have a positive correlation with the frequency. Furthermore, in FIG. 12, the amplitude enlargement rate of the horn (2)' may have a positive correlation with the frequency, the amplitude enlargement rate of the horn (4)' may have a negative correlation with the frequency, and the amplitude enlargement rate of the horn (5)' may have a positive correlation with the frequency. A vibration node that occurs at a vibration output end of the horn of the vibration transmitting member is located on the distal side by approximately a half-wavelength of ultrasonic vibration from a vibration node that occurs at a vibration input end of the horn of the BLT.

In the above-described example and the like, the correlation of the vibration speed at the vibration generator (1)' of the BLT with the frequency is a negative correlation. However, even when the correlation of the vibration speed at the vibration generator (1)' of the BLT with the frequency is a positive correlation, the slope of correlation of the vibration speed in the distal portion of the vibration transmitting member with the frequency can be made close to flat (zero) as a whole, by setting the amplitude enlargement rate at one of the horns (2)', (4)', and (5)' in such a manner that the amplitude enlargement rate has a negative correlation with the frequency, as in the above-described function. The number of horns is three in the above-described modification, but is not limited thereto.

Second Example

In the above-described modification of the first example (see FIGS. 12 and 13), when a vibration node occurs in the vicinity of the vibration input end of the horn of the vibration generating unit, a node adjacent to this vibration node occurs in the vicinity of the vibration output end of the horn of the ultrasonic probe. Instead, in the second example, a vibration node may occur in the vicinity of a vibration output end of a horn (e.g., horn (2)' in FIG. 12) of the vibration generating unit, and a node adjacent to this vibration node may occur in the vicinity of a vibration input end of a horn (e.g., horn (4)' in FIG. 12) of the vibration transmitting member (ultrasonic probe). In the present example, a vibration generating unit 22 (front mass 23) is supported by a transducer case 21 at a distal end (vibration output end) of a horn of the vibration generating unit.

Figure 14:
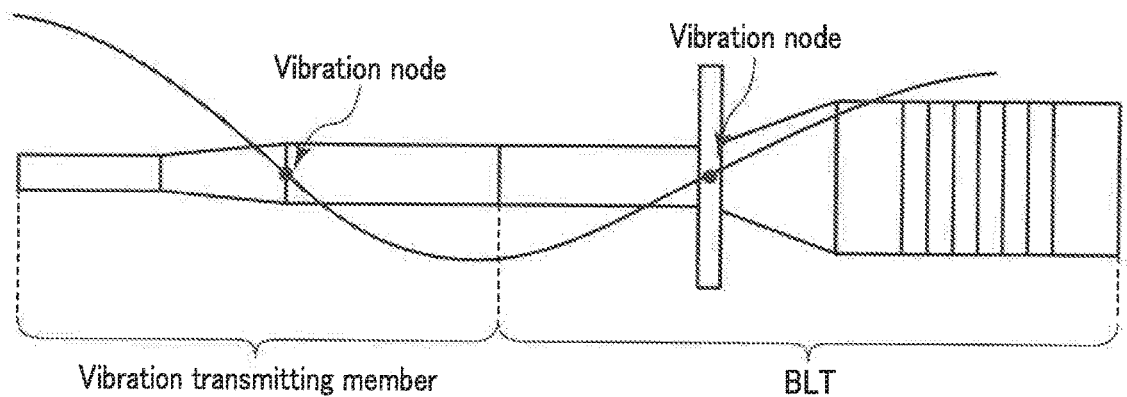
FIG. 14 is a schematic view showing an exemplary positional relationship between vibration nodes and horns according to a second example.

FIG. 14 is a schematic view showing an exemplary positional relationship between vibration nodes and horns according to the second example. As shown in FIG. 14, one of vibration nodes of ultrasonic vibration occurs at a vibration output end of a horn of a BLT, and a vibration node adjacent to this vibration node occurs at a vibration input end of a horn of a vibration transmitting member. That is, the positions of the vibration nodes of the horn of the BLT and the horn of the vibration transmitting member are opposite to those in the example shown in FIG. 13.

In the configuration of FIG. 14, too, the trend of changes in amplitude enlargement rate at the horn of the BLT relative to the frequency is opposite to the trend of changes in amplitude enlargement rate at the horn of the vibration transmitting member relative to the frequency. That is, the two horns have opposite correlations between the frequency and the amplitude enlargement rate. Thus, when viewed as a whole vibration system, the correlations act to cancel each other out. A vibration node that occurs at the vibration input end of the horn of the vibration transmitting member is located on the distal side by a half-wavelength of ultrasonic vibration from a vibration node that occurs at the vibration output end of the horn of the BLT.

According to the second example with the above-described configuration, the amplitude enlargement rate of the horn of the BLT has a positive correlation with the frequency, whereas the amplitude enlargement rate of the horn of the vibration transmitting member has a negative correlation with the frequency. It is thus possible to make the correlations of the amplitude enlargement rate with the frequency change in the horns mutually opposite to each other, and to reduce variability (fluctuation) in the vibration speed at a distal end of the vibration transmitting member relative to the frequency to a permissible range.

Third Example

Figure 15:
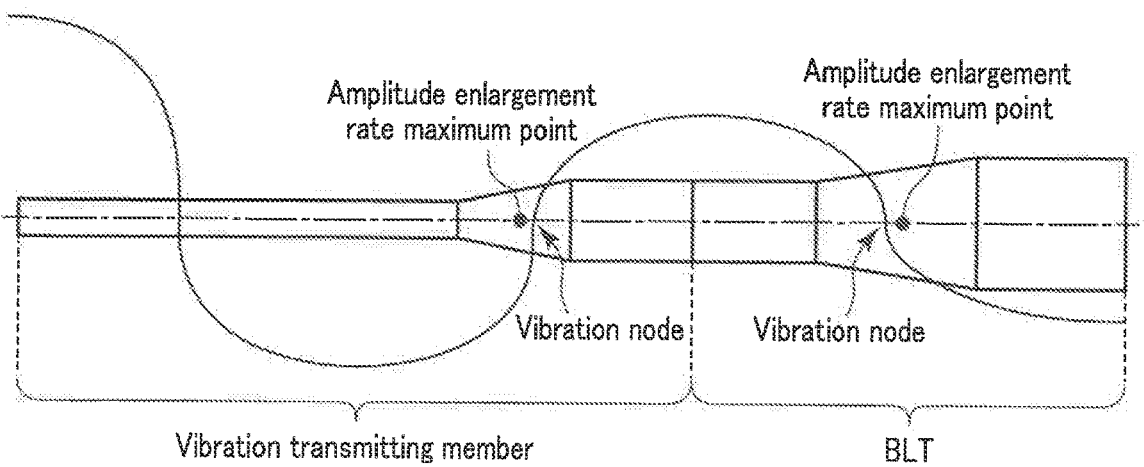
FIG. 15 shows an exemplary relationship between horns and vibration nodes according to a third example.

FIG. 15 shows an exemplary relationship between horns and vibration nodes according to the third example. A typical horn has a tapered structure whose diameter decreases from the vibration input end toward the vibration output end. There is a point where the amplitude enlargement rate becomes maximum between the vibration input end and the vibration output end. This point will be referred to as an amplitude enlargement rate maximum point. In determining the amplitude enlargement rate maximum point, an amplitude enlargement rate of an amplitude of vibration at a position on the distal side by a quarter-wavelength from that position to an amplitude of vibration at a position on the proximal side by a quarter-wavelength from that position is calculated, with respect to all the positions of the horns in a direction parallel to the longitudinal axis C (longitudinal axis direction). The position where the calculated amplitude enlargement rate becomes maximum at the horn is determined as the amplitude enlargement rate maximum point.

In the third example, consideration is given to the positional relationship between the amplitude enlargement rate maximum points and the vibration nodes, as shown in FIG. 15. In FIG. 15, let us assume that a vibration node is located on the distal side with respect to the amplitude enlargement rate maximum point in a horn (e.g., horn (2)' in FIG. 12) of a vibration generating unit. On the other hand, dimensions of each part are adjusted in such a manner that a vibration node is located on the proximal side (back mass side) with respect to the amplitude enlargement rate maximum point in a horn (e.g., horn (4)' of FIG. 12) of an ultrasonic probe (vibration transmitting member).

Figure 16:
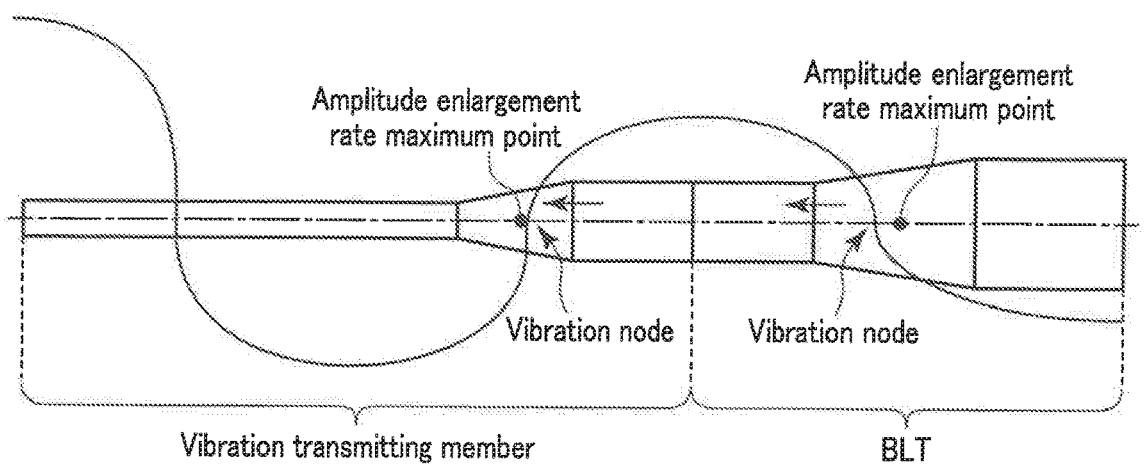
FIG. 16 shows a state in which the vibration frequency has decreased from the state shown in FIG. 15.

In the above-described configuration, let us assume that the vibration frequency of the entire vibration system has decreased from that at the time of designing, due to physical properties of the vibration transmitting member attached to the vibration generating unit. In that case, the wavelength of vibration increases, and, as shown in FIG. 16, the vibration nodes move toward the distal side (direction of the arrows in the drawing) as a whole. That is, the vibration node moves away from the amplitude enlargement rate maximum point in the horn of the vibration generating unit, whereas the vibration node moves toward the amplitude enlargement rate maximum point in the horn of the ultrasonic probe (vibration transmitting member). Thereby, the fluctuations in amplitude enlargement rate act to cancel each other out by the two horns. The fluctuations in amplitude enlargement rate are suppressed as a whole, and changes in vibration speed in the distal portion are reduced.

Figure 17:
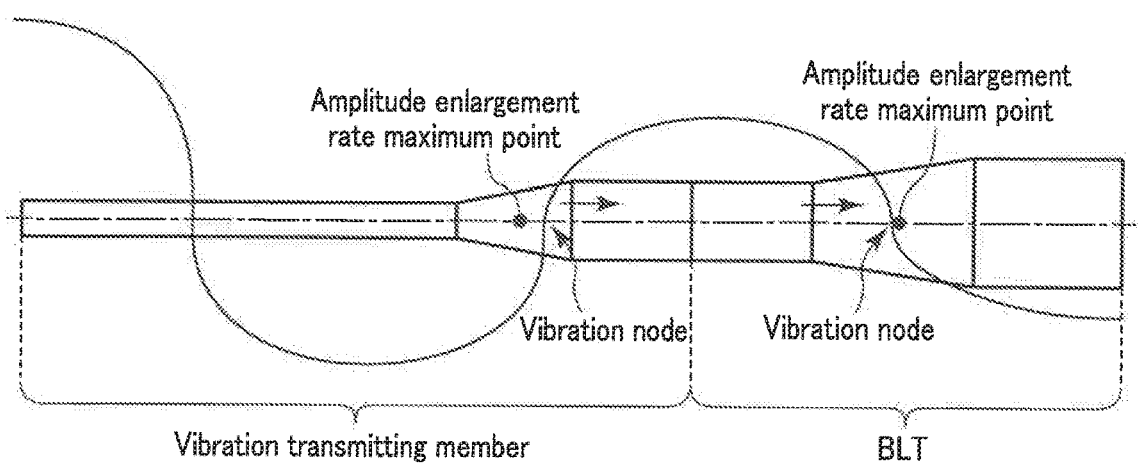
FIG. 17 shows a state in which the vibration frequency has increased from the state shown in FIG. 15.

Conversely, let us assume that the vibration frequency of the entire vibration system has increased from that at the time of designing, due to physical properties of the vibration transmitting member attached to the vibration generating unit. In that case, as shown in FIG. 17, the wavelength of vibration decreases, and the vibration nodes move toward the proximal side (direction of the arrows in the drawing) as a whole. That is, the vibration node comes close to the amplitude enlargement rate maximum point in the horn of the vibration generating unit, but the vibration node moves away from the amplitude enlargement rate maximum point in the horn of the ultrasonic probe. Thereby, the fluctuations in amplitude enlargement rate act to cancel each other out by the two horns. The fluctuations in amplitude enlargement rate are suppressed as a whole, and changes in vibration speed in the distal portion are reduced.

Thus, according to the third example, variability (fluctuation) in the vibration speed of the distal portion of the vibration transmitting portion relative to the fluctuation in frequency can be reduced to a permissible range.

Fourth Example

In the first to third example, an amplitude is enlarged by a tapered horn. Typically, an amplitude enlargement rate is proportional to the ratio of the maximum cross section to the minimum cross section of the horn. Thus, the diameter decreases in the distal portion as the desired amplitude enlargement rate increases, reducing strength. Therefore, in the fourth example, an amplitude enlargement action is achieved by joining materials with different acoustic impedances (acoustic characteristic impedances) at a vibration node.

Figure 18:
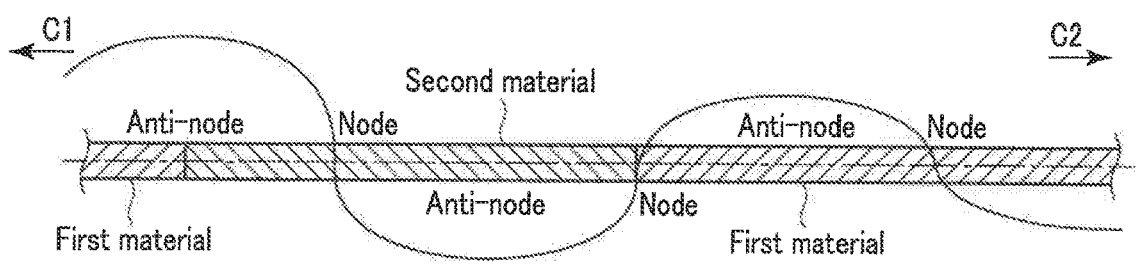
FIG. 18 is a cross-sectional view schematically showing an exemplary ultrasonic probe according to a fourth example.

FIG. 18 is a cross-sectional view schematically showing an exemplary ultrasonic probe according to a fourth example. In FIG. 18, a first material and a second material are joined at the positions of the vibration nodes. In the fourth example, the acoustic impedance of the second material is lower than the acoustic impedance of the first material. Since the acoustic impedance is expressed as $\rho cS$, where $\rho$ is the density of the material, c is the speed of sound, and S is the cross section, a material lighter than the first material, for example, can be used as the second material.

With the above-described configuration, the amplitude of ultrasonic vibration transmitted from the proximal side (side of the arrow C2) is amplified by discontinuity in acoustic impedance at the joining point between the first material and the second material, and is transmitted toward the distal side (side of the arrow C1). Thus, the amplitude enlargement effect can be obtained at the joining point between the first material and the second material, without the need to change the thickness of the vibration transmitting member. Thereby, an advantageous effect similar to those of the first to third examples may be obtained. As a matter of course, the technical idea disclosed in the fourth example may be combined with the first to third examples.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vibrating body unit comprising:
    a vibration generator which is configured to generate ultrasonic vibration, amplitude of the generated ultrasonic vibration at the vibration generator having a predetermined correlation with a frequency, the predetermined correlation being positive when the amplitude increases with an increase in frequency, or negative when the amplitude decreases with the increase in frequency;
    a vibration transmitting portion which has a proximal end and a distal end, and to which the vibration generator is attached on a proximal side, the vibration transmitting portion being configured to transmit the ultrasonic vibration to a distal side in a longitudinal axis direction; and
    a first amplitude enlarger which is provided in the vibration transmitting portion, and which is configured to enlarge the amplitude of the ultrasonic vibration at a first amplitude enlargement rate in a direction of transmission of the ultrasonic vibration, the first amplitude enlargement rate being a ratio of:
        an output amplitude at a first position on a distal side of the first amplitude enlarger, and
        an input amplitude at a second position on a proximal side of the first amplitude enlarger,
    wherein:
        a correlation between the first amplitude enlargement rate and the frequency is:
            (i) positive when the first amplitude enlargement rate increases with the increase in frequency, or (ii) negative when the first amplitude enlargement rate decreases with the increase in frequency, and the correlation between the first amplitude enlargement rate of the first amplitude enlarger and the frequency is opposite to the predetermined correlation between the generated ultrasonic vibration at the vibration generator and the frequency.

2. The vibrating body unit according to claim 1, wherein the predetermined correlation is negative, and the correlation between the first amplitude enlargement rate and the frequency is positive.

3. The vibrating body unit according to claim 2, further comprising a second amplitude enlarger which is provided in a third position different from that of the first amplitude enlarger in the vibration transmitting portion in the longitudinal axis direction, and which is configured to enlarge the amplitude of the ultrasonic vibration at a second amplitude enlargement rate in the direction of transmission of the ultrasonic vibration, a correlation between the second amplitude enlargement rate and the frequency being negative.

4. The vibrating body unit according to claim 3, wherein the second amplitude enlarger is located on the distal side with respect to the first amplitude enlarger, and the first amplitude enlarger and the second amplitude enlarger are arranged in a manner such that a first node of the ultrasonic vibration is located at the first amplitude enlarger and a second node of the ultrasonic vibration, which is located on the distal side with respect to the first node, is located in the second amplitude enlarger.

5. The vibrating body unit according to claim 4, wherein the first amplitude enlarger and the second amplitude enlarger are arranged in a manner such that the first node is located at a vibration output end of the first amplitude enlarger and the second node is located at a vibration input end of the second amplitude enlarger.

6. The vibrating body unit according to claim 4, wherein the first amplitude enlarger and the second amplitude enlarger are arranged in a manner such that the first node is located on the distal side with respect to an amplitude enlargement rate maximum point of the first amplitude enlarger and the second node is located on the proximal side with respect to an amplitude enlargement rate maximum point of the second amplitude enlarger, where the amplitude enlargement rate maximum point of the first amplitude enlarger denotes a first point where the first amplitude enlargement rate becomes a first maximum between a first vibration input end and a first vibration output end, and the amplitude enlargement rate maximum point of the second amplitude enlarger denotes a second point where the second amplitude enlargement rate becomes a second maximum between a second vibration input end and a second vibration output end.

7. The vibrating body unit according to claim 1, wherein the vibration transmitting portion includes:

a transmitting member to which the vibration generator is attached, and to which the ultrasonic vibration is transmitted from the vibration generator; and an ultrasonic probe which has a proximal end detachably connected to a distal end of the transmitting member, and which forms the distal end of the vibration transmitting portion, the ultrasonic vibration being transmitted from the vibration generator to the ultrasonic probe via the transmitting member.

8. The vibrating body unit according to claim 7, wherein the first amplitude enlarger is provided in the transmitting member, and the ultrasonic probe includes a second amplitude enlarger which is configured to enlarge the amplitude of the ultrasonic vibration at a second amplitude enlargement rate in the direction of transmission of the ultrasonic vibration, a correlation between the second amplitude enlargement rate and the frequency being negative.

9. The vibrating body unit according to claim 1, wherein the vibrating body unit is configured such that:

a first node of ultrasonic vibration occurs at a distal end of the vibration generator, and a second node of ultrasonic vibration, adjacent to the first node, occurs at a vibration output end of the first amplitude enlarger.

10. The vibrating body unit according to claim 9, wherein the second node is located on a distal side of the first node by approximately a half-wavelength of ultrasonic vibration.

11. The vibrating body unit according to claim 1, further comprising a second amplitude enlarger located in the vibration generator, wherein the vibrating body unit is configured such that:

a first node of ultrasonic vibration occurs at a vibration input end of the second amplitude enlarger, and a second node of ultrasonic vibration, adjacent to the first node, occurs at a vibration output end of the first amplitude enlarger; or the first node of ultrasonic vibration occurs at a vibration output end of the second amplitude enlarger, and the second node of ultrasonic vibration, adjacent to the first node, occurs at a vibration input end of the first amplitude enlarger.

12. The vibrating body unit according to claim 11, wherein the second node is located on a distal side of the first node by approximately a half-wavelength of ultrasonic vibration.

13. An ultrasonic probe which is separably connected to a vibration generating unit including a vibration generator, the vibration generator being configured to generate ultrasonic vibration, amplitude of the generated ultrasonic vibration at the vibration generator having a predetermined correlation with a frequency, the predetermined correlation being positive when the amplitude increases with an increase in frequency, or negative when the amplitude decreases with the increase in frequency, the ultrasonic probe comprising:

a vibration transmitting member which has a proximal end and a distal end, and which is configured to transmit, to a distal side, the ultrasonic vibration transmitted from the vibration generating unit to the proximal end in a longitudinal axis direction; and an amplitude enlarger which is provided in the vibration transmitting member, and which is configured to enlarge the amplitude of the ultrasonic vibration at an amplitude enlargement rate in a direction of transmission of the ultrasonic vibration, the amplitude enlargement rate being a ratio of:

an output amplitude at a first position on a distal side of the amplitude enlarger, and an input amplitude at a second position on a proximal side of the amplitude enlarger, wherein:

a correlation between the amplitude enlargement rate and the frequency is:

(i) positive when amplitude enlargement rate increases with the increase in frequency, or (ii) negative when the amplitude enlargement rate decreases with the increase in frequency, and the correlation between the amplitude enlargement rate of the amplitude enlarger and the frequency is opposite to the predetermined correlation between the generated ultrasonic vibration at the vibration generator and the frequency.

* * * * *